(12) United States Patent
Broome et al.

(10) Patent No.: US 7,481,823 B2
(45) Date of Patent: Jan. 27, 2009

(54) MULTIPLE MEMBRANE EMBOLIC PROTECTION FILTER

(75) Inventors: Thomas E. Broome, Shakopee, MN (US); Virgil Voeller, St. Louis Park, MN (US); Mel Beulke, Bloomington, MN (US); Anthony C. Vrba, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 477 days.

(21) Appl. No.: 10/280,191

(22) Filed: Oct. 25, 2002

(65) Prior Publication Data
US 2004/0082967 A1    Apr. 29, 2004

(51) Int. Cl.
*A61M 29/00* (2006.01)
(52) U.S. Cl. .................................................... 606/200
(58) Field of Classification Search ................ 606/200
See application file for complete search history.

(56) References Cited

U.S. PATENT DOCUMENTS

| | | | |
|---|---|---|---|
| 3,472,230 A | 10/1969 | Fogarty | |
| 3,952,747 A | 4/1976 | Kimmell, Jr. | |
| 3,996,938 A | 12/1976 | Clark, III | |
| 4,046,150 A | 9/1977 | Schwartz et al. | |
| 4,425,908 A | 1/1984 | Simon | |
| 4,590,938 A | 5/1986 | Segura et al. | |
| 4,619,246 A | 10/1986 | Molgaard-Nielsen et al. | |
| 4,650,466 A | 3/1987 | Luther | |
| 4,706,671 A | 11/1987 | Weinrib | |
| 4,723,549 A | 2/1988 | Wholey et al. | |
| 4,790,812 A | 12/1988 | Hawkins, Jr. et al. | |
| 4,790,813 A | 12/1988 | Kensey | |
| 4,794,928 A | 1/1989 | Kletschka | |
| 4,807,626 A | 2/1989 | McGirr | |
| 4,873,978 A | 10/1989 | Ginsburg | |
| 4,921,478 A | 5/1990 | Solano et al. | |
| 4,921,484 A | 5/1990 | Hillstead | |
| 4,926,858 A | 5/1990 | Gifford, III et al. | |
| 4,969,891 A | 11/1990 | Gewertz | |

(Continued)

FOREIGN PATENT DOCUMENTS

DE    28 21 048    7/1980

(Continued)

OTHER PUBLICATIONS

"Atherosclerotic Disease of the Aortic Arch as a Risk Factor of Recurrent Ischemic Stroke," *The New England Journal of Medicine*, pp. 1216-1221 (May 1996).

(Continued)

*Primary Examiner*—Todd E Manahan
*Assistant Examiner*—Tuan V Nguyen
(74) *Attorney, Agent, or Firm*—Compton Seager & Tufte LLC

(57) ABSTRACT

An embolic protection filter having a plurality of filter membranes for collecting embolic debris within a body lumen is disclosed. An embolic protection filter in accordance with an exemplary embodiment of the present invention includes a first filter membrane coupled to an elongated member, a second filter membrane coupled to the elongated member distal the first filter membrane, and an actuator mechanism for actuating the embolic protection filter within a vessel.

41 Claims, 4 Drawing Sheets

U.S. PATENT DOCUMENTS

| | | | |
|---|---|---|---|
| 4,998,539 A | 3/1991 | Delsanti | |
| 5,002,560 A | 3/1991 | Machold et al. | |
| 5,011,488 A | 4/1991 | Ginsburg | |
| 5,053,008 A | 10/1991 | Bajaj | |
| 5,071,407 A | 12/1991 | Termin et al. | |
| 5,100,423 A | 3/1992 | Fearnot | |
| 5,102,415 A | 4/1992 | Guenther et al. | |
| 5,133,733 A | 7/1992 | Rasmussen et al. | |
| 5,152,771 A | 10/1992 | Sabbaghian et al. | |
| 5,152,777 A | 10/1992 | Goldberg et al. | |
| 5,160,342 A | 11/1992 | Reger et al. | |
| 5,224,953 A | 7/1993 | Morgentaler | |
| 5,329,942 A | 7/1994 | Gunther et al. | |
| 5,330,484 A | 7/1994 | Gunther | |
| 5,354,310 A | 10/1994 | Garnie et al. | |
| 5,376,100 A | 12/1994 | Lefebvre | |
| 5,421,832 A | 6/1995 | Lefebvre | |
| 5,423,742 A | 6/1995 | Theron | |
| 5,449,372 A | 9/1995 | Schmaltz et al. | |
| 4,842,579 A | 10/1995 | Shiber | |
| 5,456,667 A | 10/1995 | Ham et al. | |
| 5,462,529 A | 10/1995 | Simpson et al. | |
| 5,536,242 A | 7/1996 | Willard et al. | |
| 5,549,626 A | 8/1996 | Miller et al. | |
| 5,658,296 A | 8/1997 | Bates et al. | |
| 5,662,671 A | 9/1997 | Barbut et al. | |
| 5,695,519 A | 12/1997 | Summers et al. | |
| 5,720,764 A | 2/1998 | Naderlinger | |
| 5,728,066 A | 3/1998 | Daneshvar | |
| 5,749,848 A | 5/1998 | Jang et al. | |
| 5,769,816 A | 6/1998 | Barbut et al. | |
| 5,779,716 A | 7/1998 | Cano et al. | |
| 5,792,157 A | 8/1998 | Mische et al. | |
| 5,795,322 A | 8/1998 | Bouewijn | |
| 5,800,457 A | 9/1998 | Gelbfish | |
| 5,800,525 A | 9/1998 | Bachinski et al. | |
| 5,810,874 A | 9/1998 | Lefebvre | |
| 5,814,064 A | 9/1998 | Daniel et al. | |
| 5,827,324 A | 10/1998 | Cassell et al. | |
| 5,833,644 A | 11/1998 | Zadno-Azizi et al. | |
| 5,833,650 A | 11/1998 | Imran | |
| 5,846,260 A | 12/1998 | Maahs | |
| 5,848,964 A | 12/1998 | Samuels | |
| 5,876,367 A | 3/1999 | Kaganov et al. | |
| 5,895,399 A | 4/1999 | Barbut et al. | |
| 5,910,154 A | 6/1999 | Tsugita et al. | |
| 5,911,734 A | 6/1999 | Tsugita et al. | |
| 5,925,016 A | 7/1999 | Chornenky et al. | |
| 5,925,060 A | 7/1999 | Forber | |
| 5,925,062 A | 7/1999 | Purdy | |
| 5,935,139 A | 8/1999 | Bates | |
| 5,941,869 A | 8/1999 | Patterson et al. | |
| 5,941,896 A | 8/1999 | Kerr | |
| 5,947,995 A | 9/1999 | Samuels | |
| 5,954,745 A | 9/1999 | Gertler et al. | |
| 5,980,555 A | 11/1999 | Barbut et al. | |
| 5,989,281 A | 11/1999 | Barbut et al. | |
| 5,993,469 A | 11/1999 | McKenzie et al. | |
| 5,997,557 A | 12/1999 | Barbut et al. | |
| 6,001,118 A | 12/1999 | Daniel et al. | |
| 6,007,557 A | 12/1999 | Ambrisco et al. | |
| 6,010,522 A | 1/2000 | Barbut et al. | |
| 6,013,085 A | 1/2000 | Howard | |
| 6,027,520 A | 2/2000 | Tsugita et al. | |
| 6,042,598 A | 3/2000 | Tsugita et al. | |
| 6,051,014 A | 4/2000 | Jang | |
| 6,051,015 A | 4/2000 | Maahs | |
| 6,053,932 A | 4/2000 | Daniel et al. | |
| 6,059,814 A | 5/2000 | Ladd | |
| 6,066,149 A | 5/2000 | Samson et al. | |
| 6,066,158 A | 5/2000 | Engelson et al. | |
| 6,068,645 A | 5/2000 | Tu | |
| 6,086,605 A | 7/2000 | Barbut et al. | |
| 6,117,154 A | 9/2000 | Barbut et al. | |
| 6,129,739 A | 10/2000 | Khosravi | |
| 6,136,016 A | 10/2000 | Barbut et al. | |
| 6,142,987 A | 11/2000 | Tsugita | |
| 6,152,946 A | 11/2000 | Broome et al. | |
| 6,165,200 A | 12/2000 | Tsugita et al. | |
| 6,168,579 B1 | 1/2001 | Tsugita | |
| 6,171,327 B1 | 1/2001 | Daniel et al. | |
| 6,171,328 B1 | 1/2001 | Addis | |
| 6,179,851 B1 | 1/2001 | Barbut et al. | |
| 6,179,859 B1 | 1/2001 | Bates et al. | |
| 6,179,861 B1 | 1/2001 | Khosravi et al. | |
| 6,203,561 B1 | 3/2001 | Ramee et al. | |
| 6,206,868 B1 | 3/2001 | Parodi | |
| 6,214,026 B1 | 4/2001 | Lepak et al. | |
| 6,221,006 B1 | 4/2001 | Dubrul et al. | |
| 6,224,620 B1 | 5/2001 | Maahs | |
| 6,231,544 B1 | 5/2001 | Tsugita et al. | |
| 6,235,044 B1 | 5/2001 | Root et al. | |
| 6,235,045 B1 | 5/2001 | Barbut et al. | |
| 6,238,412 B1 | 5/2001 | Dubrul et al. | |
| 6,245,087 B1 | 6/2001 | Addis | |
| 6,245,088 B1 | 6/2001 | Lowery | |
| 6,245,089 B1 | 6/2001 | Daniel et al. | |
| 6,258,115 B1 | 7/2001 | Dubrul | |
| 6,264,663 B1 | 7/2001 | Cano | |
| 6,264,672 B1 | 7/2001 | Fisher | |
| 6,270,513 B1 | 8/2001 | Tsugita et al. | |
| 6,277,138 B1 | 8/2001 | Levinson et al. | |
| 6,277,139 B1 | 8/2001 | Levinson et al. | |
| 6,280,413 B1 | 8/2001 | Clark et al. | |
| 6,287,321 B1 | 9/2001 | Jang | |
| 6,290,710 B1 | 9/2001 | Cryer et al. | |
| 6,309,399 B1 | 10/2001 | Barbut et al. | |
| 6,319,268 B1 | 11/2001 | Ambrisco et al. | |
| 6,344,049 B1 | 2/2002 | Levinson et al. | |
| 6,391,044 B1 * | 5/2002 | Yadav et al. | 606/200 |
| 6,511,497 B1 * | 1/2003 | Braun et al. | 606/200 |
| 6,520,978 B1 * | 2/2003 | Blackledge et al. | 606/200 |
| 2002/0161390 A1 * | 10/2002 | Mouw | 606/200 |
| 2004/0267302 A1 * | 12/2004 | Gilson et al. | 606/200 |

FOREIGN PATENT DOCUMENTS

| | | |
|---|---|---|
| DE | 34 17 738 | 11/1985 |
| DE | 40 30 998 A1 | 10/1990 |
| DE | 199 16 162 | 10/2000 |
| EP | 0 200 688 | 11/1986 |
| EP | 0 293 605 A1 | 12/1988 |
| EP | 0 411 118 A1 | 2/1991 |
| EP | 0 427 429 A2 | 5/1991 |
| EP | 0 437 121 B1 | 7/1991 |
| EP | 0 472 334 A1 | 2/1992 |
| EP | 0 472 368 A2 | 2/1992 |
| EP | 0 533 511 A1 | 3/1993 |
| EP | 0 655 228 A1 | 11/1994 |
| EP | 0 686 379 A2 | 6/1995 |
| EP | 0 696 447 A2 | 2/1996 |
| EP | 0 737 450 A1 | 10/1996 |
| EP | 0 743 046 A1 | 11/1996 |
| EP | 0 759 287 A1 | 2/1997 |
| EP | 0 771 549 A2 | 5/1997 |
| EP | 0 784 988 A1 | 7/1997 |
| EP | 0 852 132 A1 | 7/1998 |
| EP | 1 127 556 A2 | 8/2001 |
| FR | 2 580 504 | 10/1986 |
| FR | 2 643 250 A1 | 8/1990 |
| FR | 2 666 980 | 3/1992 |
| FR | 2 694 687 | 8/1992 |
| FR | 2 768 326 A1 | 3/1999 |
| GB | 2 020 557 B | 1/1993 |

| | | |
|---|---|---|
| JP | 8-187294 A | 7/1996 |
| SU | 764684 | 9/1980 |
| WO | WO 88/09683 | 12/1988 |
| WO | WO 92/03097 | 3/1992 |
| WO | WO 94/14389 | 7/1994 |
| WO | WO 94/24946 | 11/1994 |
| WO | WO 96/01591 | 1/1996 |
| WO | WO 96/10375 | 4/1996 |
| WO | WO 96/19941 | 7/1996 |
| WO | WO 96/23441 | 8/1996 |
| WO | WO 96/33677 | 10/1996 |
| WO | WO 97/17100 | 5/1997 |
| WO | WO 97/27808 | 8/1997 |
| WO | WO 97/42879 | 11/1997 |
| WO | WO 98/02084 | 1/1998 |
| WO | WO 98/02112 | 1/1998 |
| WO | WO 98/23322 | 6/1998 |
| WO | WO 98/33443 | 8/1998 |
| WO | WO 98/34673 | 8/1998 |
| WO | WO 98/36786 | 8/1998 |
| WO | WO 98/38920 | 9/1998 |
| WO | WO 98/38929 | 9/1998 |
| WO | WO 98/39046 | 9/1998 |
| WO | WO 98/39053 | 9/1998 |
| WO | WO 98/46297 | 10/1998 |
| WO | WO 98/47447 | 10/1998 |
| WO | WO 98/49952 | 11/1998 |
| WO | WO 98/50103 | 11/1998 |
| WO | WO 98/51237 | 11/1998 |
| WO | WO 98/55175 | 12/1998 |
| WO | WO 99/09895 | 3/1999 |
| WO | WO 99/22673 | 5/1999 |
| WO | WO 99/23976 | 5/1999 |
| WO | WO 99/25252 | 5/1999 |
| WO | WO 99/30766 | 6/1999 |
| WO | EP 0 934 729 | 8/1999 |
| WO | WO 99/40964 | 8/1999 |
| WO | WO 99/42059 | 8/1999 |
| WO | WO 99/44510 | 9/1999 |
| WO | WO 99/44542 | 9/1999 |
| WO | WO 99/55236 | 11/1999 |
| WO | WO 99/58068 | 11/1999 |
| WO | WO 00/07521 | 2/2000 |
| WO | WO 00/07655 | 2/2000 |
| WO | WO 00/09054 | 2/2000 |
| WO | WO 00/16705 | 3/2000 |
| WO | WO 00/49970 | 8/2000 |
| WO | WO 00/53120 | 9/2000 |
| WO | WO 00/67664 | 11/2000 |
| WO | WO 00/67665 | 11/2000 |
| WO | WO 00/67666 | 11/2000 |
| WO | WO 00/67668 | 11/2000 |
| WO | WO 00/67669 | 11/2000 |
| WO | WO 01/05462 | 1/2001 |
| WO | WO 01/08595 | 2/2001 |
| WO | WO 01/08596 | 2/2001 |
| WO | WO 01/08742 | 2/2001 |
| WO | WO 01/08743 | 2/2001 |
| WO | WO 01/10320 | 2/2001 |
| WO | WO 01/15629 | 3/2001 |
| WO | WO 01/21077 | 3/2001 |
| WO | WO 01/21100 | 3/2001 |
| WO | WO 01/26726 | 4/2001 |
| WO | WO 01/35857 | 5/2001 |
| WO | WO 01/43662 | 6/2001 |
| WO | WO 01/47579 | 7/2001 |
| WO | WO 01/49208 | 7/2001 |
| WO | WO 01/49209 | 7/2001 |
| WO | WO 01/49215 | 7/2001 |
| WO | WO 01/49355 | 7/2001 |
| WO | WO 01/52768 | 7/2001 |
| WO | WO 01/58382 | 8/2001 |
| WO | WO 01/60442 | 8/2001 |
| WO | WO 01//67989 | 9/2001 |
| WO | WO 01/70326 | 9/2001 |
| WO | WO 01/72205 | 10/2001 |
| WO | WO 01/87183 | 11/2001 |
| WO | WO 01/89413 | 11/2001 |
| WO | WO 01/91824 | 12/2001 |

OTHER PUBLICATIONS

"Endovascular Grafts, Stents Drive Interventional Radiology Growth," *Cardiovascular Device Update*, 2(3):1-12 (Mar. 1996).
"Protruding Atheromas in the Thoracic Aortic and Systemic Embolization," pp. 423-427 American College of Physicians (1991).
"Recognition and Embolic Potential of Intraaortic Atherosclerotic Debris," American College of Cardiology (Jan. 1991).
Cragg, Andrew et al., "A New Percutaneous Vena Cava Filger," *AJR*, 141:601-604 (Sep. 1983).
Cragg, Andrew et al., "Nonsurgical Placement of Arterial Endoprosthesis: A New Technique Using Nitinol Wire," AJR, pp. 261-263 (Apr. 1983).
Diethrich et al., "Percutaneous Techniques for Endoluminal Carotid Interventions," *J. Endovasc. Surg.*, 3:182-202 (1996).
Fadali, A. Moneim, "A filtering device for the prevention of particulate embolization during the course of cardiac surgery," *Surgery*, 64(3):634-639 (Sep. 1968).
Haissaguerre et al., "Spontaneous Initiation of Atrial Fibrillation by Ectopic Beats Originating in the Pulmonary Veins," *The New England Journal of Medicine*, 339(10):659-666 (Sep. 1988).
Jordan, Jr. et al., "Microemboli Detected by Transcranial Doppler Monitoring . . . ," *Cardiovascular Surgery*, 7(1)33-38 (Jan. 1999).
Lesh, "Can Catheter Ablation Cure Atrial Fibrillation?" *ACC Current Journal Review*, pp. 38-40 (Sep./Oct. 1997).
Lund et al., "Long-Term Patentcy of Ductus Arteriosus After Balloon Dilation: an Experimental Study," *Laboratory Investigation*, 69(4):772-774 (Apr. 1984).
Marache et al., "Percutaneous Transluminal Venous Angioplasty . . . ," *American Heart Journal*, 125(2 Pt 1):362-366 (Feb. 1993).
Mazur et al., "Directional Atherectomy with the Omnicath™: A Unique New Catheter System," *Catheterization and Cardiovascular Diagnosis*, 31:17-84 (1994).
Moussa, MD, Issaam "Stents Don't Require Systemic Anticoagulation . . . But the Technique (and Results) Must be Optimal," *Journal of Invasive Cardiol.*, 8(E):3E-7E, (1996).
Nakanishi et al., "Catheter Intervention to Venous System Using Expandable Metallic Stents," *Rinsho Kyobu Geka*, 14(2):English Abstract Only (Apr. 1994).
Onal et al., "Primary Stenting for Complex Atherosclerotic Plaques in Aortic and Iliac Stenoses," *Cardiovascular & Interventional Radiology*, 21(5):386-392 (1998).
Theron et al., "New Triple Coaxial Catheter System for Carotid Angioplasty with Cerebral Protection," *American Journal of Neuroradiology*, 11:869-874 (1990).
Tunick et al., "Protruding atherosclerotic plaque in the aortic arch of patients with systemic embolization: A new finding seen by transesophageal echocardiography," *American Heart Journal 120*(3):658-660 (Sep. 1990).
Waksman et al., "Distal Embolization is Common After Directional Atherectomy . . . ," *American Heart Journal*, 129(3):430-435 (1995).
Wholey, Mark H. et al., PTA and Stents in the Treatment of Extracranial Circulation, *The Journal of Invasive Cardiology*, 8(E):25E-30E (1996).

* cited by examiner

MULTIPLE MEMBRANE EMBOLIC PROTECTION FILTER

FIELD OF THE INVENTION

The present invention relates generally to the field of embolic protection devices. More specifically, the present invention pertains to embolic protection filters having multiple filter membranes for collecting embolic debris.

BACKGROUND OF THE INVENTION

Embolic protection filters are frequently utilized in combination with therapeutic devices such as revascularization catheters and stents to collect embolic debris dislodged into a patient's vasculature. In a common application such as percutaneous transluminal angioplasty (PTA) or percutaneous transluminal coronary angioplasty (PTCA), an embolic protection filter is advanced along a guidewire to a location distal a lesion or other stenosis within a vessel. Once in place, an angioplasty catheter is then advanced along the guidewire to the site of the lesion to perform the procedure. A dilatation device such as an angioplasty balloon or extraction laser is then engaged, dislodging the embolic debris from the vessel wall. The dislodged embolic debris then enters the bloodstream, and flows downstream towards the distal vasculature where it is collected and stored by the embolic protection filter.

In a typical embolic protection filter, a filter membrane is attached to a filter frame or other support means to support the filter membrane within the patient's vessel.

The filter membrane may comprise a single membrane having several openings or pores adapted to collect and store embolic debris contained within the blood while permitting the flow of blood through the embolic protection filter. Depending on the amount of embolic debris dislodged during the procedure, the openings or pores may become partially or fully occluded, causing the flow of blood within the vessel to diminish.

When this occurs, a replacement filter may need to be advanced to the site in order to replace the occluded filter. In some cases, the guidewire used to transport the device may require removal from the patient's vessel prior to insertion of the replacement filter.

SUMMARY OF THE INVENTION

The present invention relates generally to the field of embolic protection devices.

More specifically, the present invention pertains to embolic protection filters having multiple filter membranes for collecting embolic debris. In an exemplary embodiment of the present invention, an embolic protection filter includes a first filter membrane coupled to an elongated member, a second filter membrane coupled to the elongated member distal the first filter membrane, and an actuator mechanism for collapsing the first filter membrane inwardly to permit the second filter membrane to collect embolic debris once the first filter membrane has become occluded. In certain implementations, the actuator mechanism may include one or more wires coupled to the first and second filter membranes. In other implementations, the actuator mechanism may include a holding tube that can be advanced along the elongated member to radially collapse the first filter membrane.

In another exemplary embodiment, an embolic protection filter in accordance with the present invention comprises a first filter membrane coupled to an elongated member, a second filter membrane coupled to the elongated member distal the first filter membrane, and an actuator mechanism configured to rotate the first filter membrane relative to the second filter membrane. In a first position, the first filter membrane and second filter membrane can be positioned such that the openings on the first filter membrane are misaligned with the openings on the second filter membrane. Once the first filter membrane becomes occluded with embolic debris, the first filter membrane can be rotated to a second position such that the openings on the first filter membrane are aligned with the openings on the second filter membrane.

In certain embodiments, the size of the openings on the first filter membrane may be larger than the size of the openings on the second filter membrane. In use, the rotation of the first filter membrane from a first (i.e. misaligned) position to a second (i.e. aligned) position increases the overall porosity of the filter.

DETAILED DESCRIPTION OF THE INVENTION

The following description should be read with reference to the drawings, in which like elements in different drawings are numbered in like fashion. The drawings, which are not necessarily to scale, depict selected embodiments and are not intended to limit the scope of the invention. Although examples of construction, dimensions, and materials are illustrated for the various elements, those skilled in the art will recognize that many of the examples provided have suitable alternatives that may be utilized.

Figure 1:
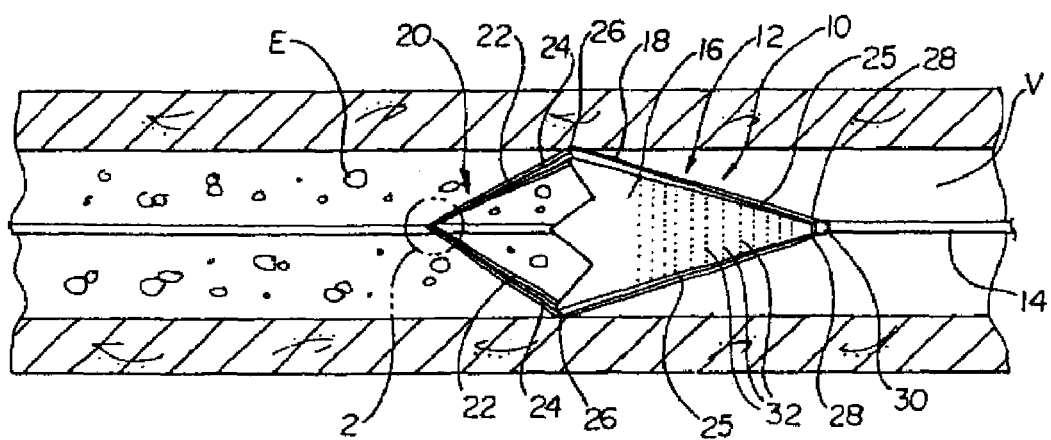
FIG. 1 is a partial cut-away view of an embolic protection filter in accordance with an exemplary embodiment of the present invention.

FIG. 1 is a partial cut-away view of an embolic protection filter 10 in accordance with an exemplary embodiment of the present invention. Embolic protection filter 10 comprises a first filter membrane 16 coupled to an elongated member 14, a second filter membrane 18 coupled to the elongated member 14 distal the first filter membrane 16, and an actuator mechanism 20. The first and second filter membranes 16, 18 can be configured in size and shape to conform to the walls of vessel V, thereby preventing the embolic debris E from traveling towards the distal vaseulature. As is discussed in greater detail below, the actuator mechanism 20 may include several retrieval members 22, 24 that can be engaged to collapse the first filter membrane 16 and second filter membrane 18 within vessel V.

Although the embolic protection filter 10 illustrated in FIG. 1 is substantially concentric along the longitudinal axis of elongated member 14, it is to be understood that other filter types can be employed without deviating from the scope of the invention. For example, a "cartridge-type" filter having multiple filter membranes located to one side of the elongated member may be employed.

Embolic protection filter 10 further comprises a filter frame 12 adapted to support the first and second filter membranes 16, 18 in a deployed position within vessel V. Filter frame 12 includes a plurality of support struts 25 each having a proximal end 26 and a distal end 28. The proximal end 26 of each support strut 25 is attached to a corresponding one of the retrieval members 22,24. The distal end 28 of each support strut 25, in turn, is attached to a rube segment 30 configured to receive the elongated member 14.

In the exemplary embodiment illustrated in FIG. 1, the plurality of support struts 25 are biased in an outward direction to stretch the filter membranes 16, 18 across the vessel V. Each support strut 25 may be formed of a bendable material such as stainless steel or platinum, or a super-elastic material such as nickel-titanium alloy (Nitinol). It is contemplated, however, that other biocompatible materials can be used to bias the support struts 25 in an outward direction.

In certain embodiments, the tube segment 30 may have an inner diameter that is slightly larger than the outer diameter of the elongated member 14, allowing the embolic protection filter 10 to slide and rotate about the elongated member 14. An optional coating (e.g. polytetraflouroethylene (PTFE)) may be applied to the inner surface of the tube segment 30 and/or to the elongated member 14 to facilitate movement of the embolic protection filter 10 along the elongated member 14.

In other embodiments, the tube segment 30 may be secured to the elongated member 14 to prevent movement of the embolic protection filter 10 thereon. Tube segment 30 can be secured to the elongated member 14 by any number of suitable attachment means, including crimping, soldering, brazing, welding, bonding, or any combination thereof. In one exemplary embodiment, a distal stop can be placed on a distal portion of the elongated member 14 to prevent movement of the embolic protection filter 10 distal the stop. In use, the stop prevents the operator from advancing the embolic protection filter 10 along the elongated member 14 distally thereof.

To prevent damage to the walls of the vessel during deployment, embolic protection filter 10 may include an anti-inflammatory agent such as dexamethasone, prednisolone, corticosterone, budesonide, estrogen, sulfasalazine, mesalamine, or any suitable combination or mixture thereof. An anti-thrombogenic coating such as heparin, urokinase or dextrophenylalanine proline arginine chloromethylketone can also be applied to the embolic protection filter 10 to prevent the formation of clots within the vasculature.

The first filter membrane 16 and second filter membrane 18 can comprise a microporous membrane formed from a polymeric material. Examples of suitable polymeric materials include polypropylene (PP), polyvinylchloride (PVC), polyamide (nylon), polyurethane, polyester, polyethylene tetraphlalate, polyether-ether ketone (PEEK), polyether block amide (PEBA), polytetraflouroethylene (PTFE), or any mixture, blend or combination thereof. Alternatively, the first and second filter membranes 16, 18 can comprise a woven or braided mesh screen made from a metallic material such as stainless steel or nickel-titanium alloy.

Several openings or pores 32 disposed on the first and second filter membranes 16,18 permit the perfusion of blood through the embolic protection filter 10. The openings 32 can be configured in size and shape to capture embolic debris while maintaining the flow of blood in the vessel. For example, the openings 32 can be circular, elliptical or rectangular in shape, and can be configured to collect embolic debris (e.g. plaque or thrombus) of varying sizes.

In certain implementations, the openings 32 can be arranged at equidistant intervals such that the openings 32 on the first filter membrane 16 can be aligned with the openings 32 on the second filter membrane 18. Alternatively, the openings 32 can be staggered such that the openings 32 on the first filter membrane 16 are misaligned with the openings or pores 32 on the second filter membrane 18.

Actuator mechanism 20 comprises a first set of retrieval members 22 connected to the first filter membrane 16, and a second set of retrieval members 24 connected to the second filter membrane 18. In the exemplary embodiment illustrated in FIG. 1, the first and second set of retrieval members 22, 24 are formed of one or more wires that can be selectively engaged to collapse the first and second filter membranes 16, 18 within the vessel V.

Figure 2:
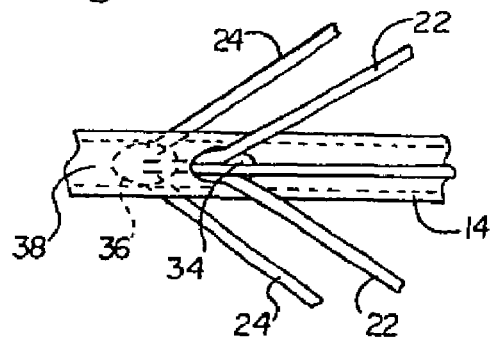
FIG. 2 is an exploded view of the actuator mechanism of FIG. 1.

FIG. 2 is an exploded view of the embolic protection filter 10 of FIG. 1, showing the connection of the first and second set of retrieval members 20, 22 to the elongated member 14. As can be seen from FIG. 2, elongated member 14 includes a first opening 34 configured to receive the first set of retrieval members 22, and a second opening 36 disposed on the opposite side of the elongated member 14 configured to receive the second set of retrieval members 24. The first and second set of retrieval members 22, 24 extend proximally within the inner lumen 38 formed by elongated member 14 to a location outside of the patient's body.

In the particular view illustrated in FIG. 1, the first filter membrane 16 and second filter membrane 18 are both shown in a deployed position within vessel V. In this position, a therapeutic procedure such as percutaneous transluminal coronary angioplasty (PTCA) can be performed at a location proximal (i.e. upstream) the embolic protection filter 10. The elongated member 14 (e.g. a guidewire, hypo-tube or catheter shaft) can be used to advance the embolic protection filter 10 to a desired location distal a lesion or other stenosis within vessel V.

Figure 3:
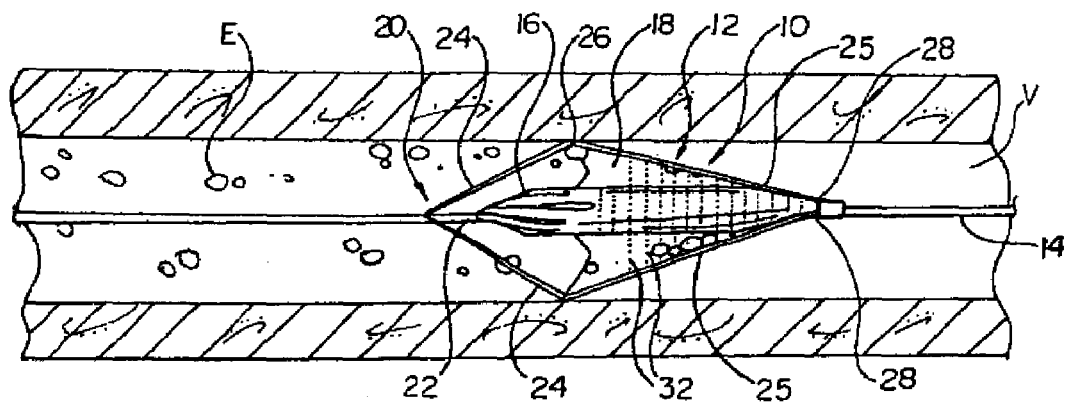
FIG. 3 is another partial cut-away view of the embolic protection filter of FIG. 1, wherein the first filter membrane is at least partially collapsed.

During the therapeutic procedure, embolic debris E dislodged from the walls of vessel V is carried distally towards the embolic protection filter 10. As the embolic debris E enters the embolic protection filter 10, it is initially collected and stored within the first filter membrane 16. Once the first filter membrane 16 becomes occluded, the operator can pull the first set of retrieval members 22 proximally, causing the first filter membrane 16 to radially collapse, as shown in FIG. 3. Once the first filter membrane 16 is collapsed, the embolic debris E can be collected and stored in the second filter membrane 18, allowing the operator to continue the therapeutic procedure without having to remove the embolic protection filter 10 or elongated member 14 from the vessel V.

Once the second filter membrane 18 has become occluded, or once the therapeutic procedure is complete, the operator can then retract the second set of retrieval members 24 proximally, causing the second filter membrane 18 to collapse. A retrieval sheath or other retrieval means can then be advanced to the site to recover the occluded embolic protection filter 10.

Figure 4:
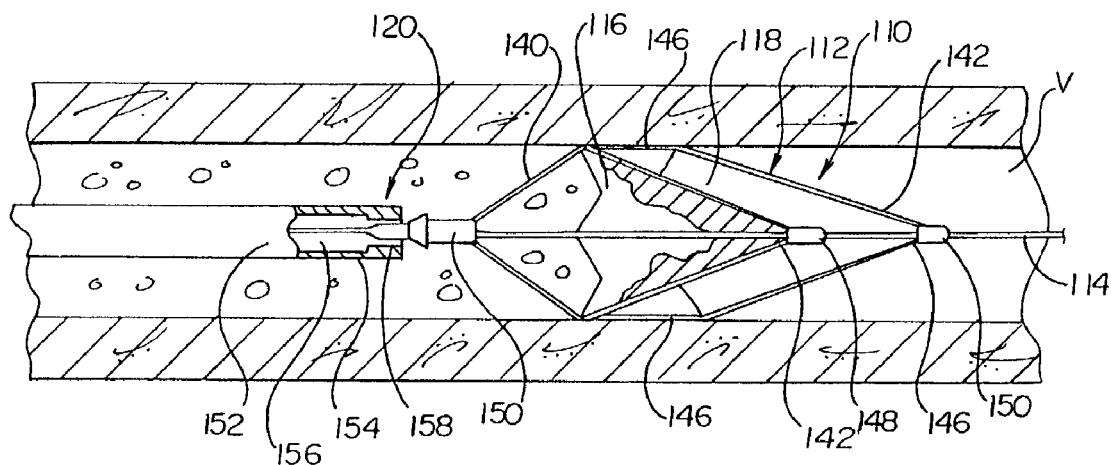
FIG. 4 is a partial cut-away view of an embolic protection filter in accordance with another exemplary embodiment of the present invention.

FIG. 4 illustrates another exemplary embodiment of an embolic protection filter 110 in accordance with the present invention. Embolic protection filter 110 comprises a first filter membrane 116 coupled to an elongated member 114, a second filter membrane 118 coupled to the elongated member 114 distal the first filter membrane 116, and an actuator mechanism 120 that can be advanced along elongated member 114 to radially collapse the first filter membrane 116.

Embolic protection filter 110 further includes a filter frame 112 adapted to support the first and second filter membranes 116, 118 in a deployed position within vessel V. Filter frame 112 includes a first set of support struts 140 coupled to the first filter membrane 116, and a second set of support struts 142 coupled to the second filter membrane 118. The distal end 144 of each of the first support struts 140 is attached to a first tube segment 148 disposed about the elongated member 114. The distal end 146 of each of the second support struts 142, in turn, is attached to a second tube segment 150 disposed about the elongated member 114 distal the first tube segment 148. The first and second tube segments 148,150 each have an inner diameter that is slightly larger than the outer diameter of the elongated member 114, allowing the embolic protection filter 110 to slide and rotate about the elongated member 114.

The first and second set of support struts 140, 142 are each biased in an outward direction such that the first and second filter membranes 116, 118 self-deploy within vessel V when unconstrained radially. A connecting member 146 connects the second set of support struts 142 to the first set of supports struts 140. As with the previous embodiment, each of the supports struts 140, 142 may be formed of a bendable material such as stainless steel or platinum, or a super-elastic material such as Nitinol.

Embolic protection filter 110 further comprises an actuator mechanism 120 slidably disposed along the elongated member 114. Actuator mechanism 120 comprises a tubular member 152 having a proximal portion (not shown), a distal portion 154, and an inner lumen 156. The distal portion 154 of actuator mechanism 120 includes a reduced inner diameter portion 158 configured in size and shape to engage a barb 160 attached to first set of support struts 140.

Figure 5:
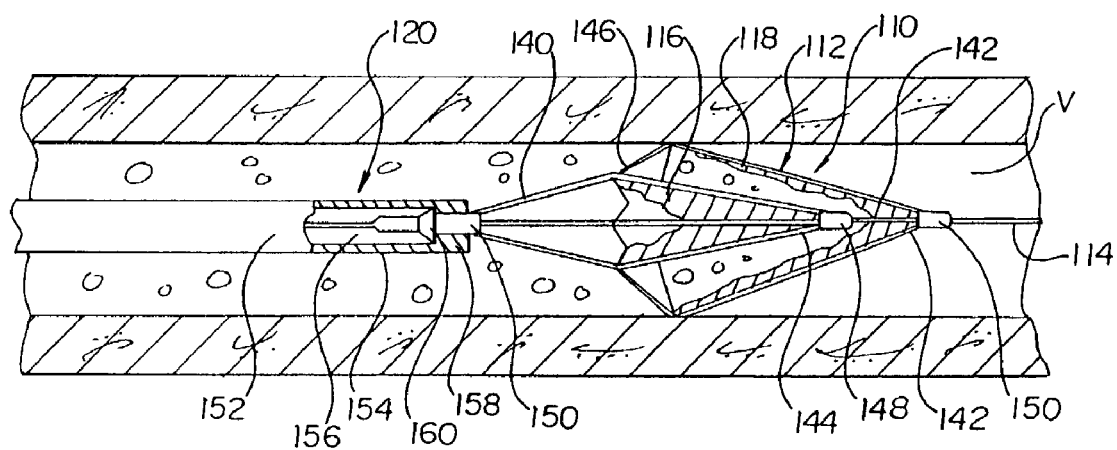
FIG. 5 is another partial cut-away view of the embolic protection filter of FIG. 4, wherein the first filter membrane is at least partially collapsed.

In a first position illustrated in FIG. 4, the first filter membrane 116 and second filter membrane 118 are fully deployed within vessel V. As the embolic debris E enters the embolic protection filter 110, it is initially collected and stored in the first filter membrane 116. Once the first filter membrane 116 becomes occluded with the embolic debris E, the operator can advance the actuator mechanism 120 along the elongated member 114 to a location proximate and proximal the barb 160. Once in position, the operator, while holding the actuator mechanism 120 stationary within vessel V, pulls the elongated member 114 proximally, forcing the barb 160 to retract beyond the reduced inner diameter portion 158. As the barb 160 is retracted into the tubular member 152, the first filter membrane 116 collapses at least in part within vessel V, allowing the embolic debris E to flow into the second filter membrane 118, as shown in FIG. 5. Once the second filter membrane 118 becomes occluded, or once the therapeutic procedure is complete, the operator can then retract the first and second filter membranes 116, 118 into the inner lumen 156 of tubular member 152. Alternatively, a separate retrieval sheath (not shown) can be advanced to the site to recover the occluded embolic protection filter 110.

Figure 6:
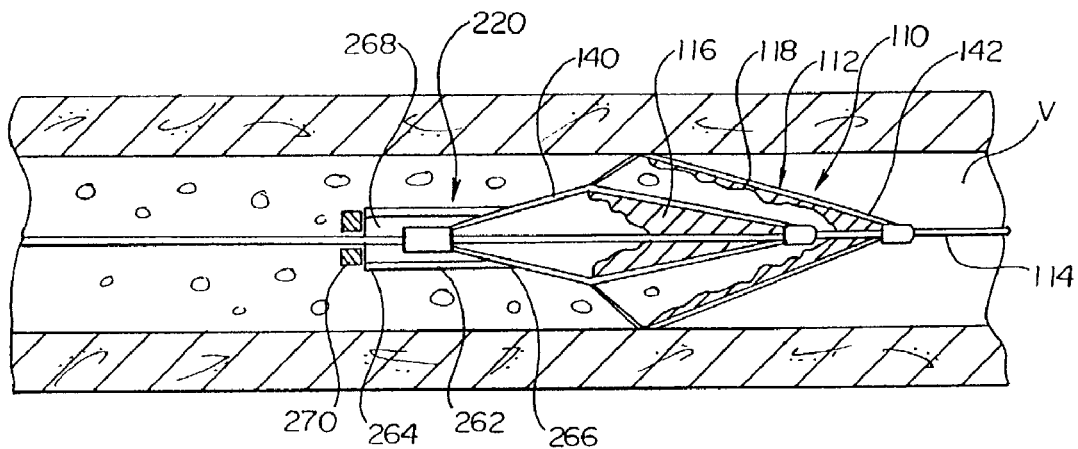
FIG. 6 is a partial cut-away view of an alternative actuator mechanism in accordance with an exemplary embodiment of the present invention utilizing a holding tube.

FIG. 6 illustrates an alternative actuator mechanism 220 in accordance with an exemplary embodiment of the present invention. Actuator mechanism 220 comprises a holding tube 262 having a proximal end 264, a distal end 266, and an inner lumen 268 configured to slidably receive the elongated member 114. In use, holding tube 262 can be advanced distally along the elongated member 114 to a point proximate and proximal a deflectable stop 270. Continued advancement of the holding tube 262 distally, or in the alternative, retraction of the elongated member 114 proximally, causes the deflectable stop 270 to bend slightly and permit the holding tube 262 to be advanced thereon. As the holding tube 262 is advanced distally beyond the deflectable stop 270, the first filter membrane 116 collapses at least in part within the inner lumen 268 of holding tube 262, allowing the embolic debris E to flow into the second filter membrane 118, as shown in FIG. 6.

Figure 7:
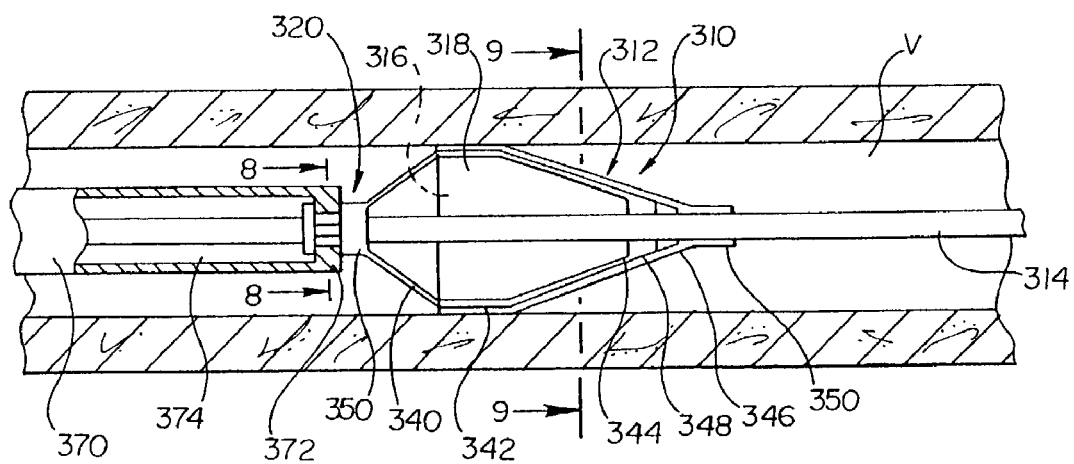
FIG. 7 is a partial cut-away view of an embolie protection filter in accordance with yet another exemplary embodiment of the present invention.

FIG. 7 illustrates yet another exemplary embodiment of an embolic protection filter 310 in accordance with the present invention. Embolic protection filter 310 comprises a first filter membrane 316 coupled to an elongated member 314, a second filter membrane 318 coupled to the elongated member 314 distal the first filter membrane 316, and an actuator mechanism 320. The actuator mechanism 320 is configured to releasably lock onto a filter base 350, allowing operator to actuate the embolic protection filter 310 between a first (i.e. misaligned) position, and a second (i.e. aligned) position.

Embolic protection filter 310 includes a filter frame 312 adapted to support the first and second filter membranes 316, 318 in a deployed position within vessel V. Filter frame 312 comprises a first set of support struts 340 coupled to the first filter membrane 316, and a second set of support struts 342 coupled to the second filter membrane 318. The distal end 344 of each of the first support struts 340 is attached to a first tube segment 348 disposed about the elongated member 314. The distal end 346 of each of the second support struts 342 is attached to a second tube segment 350 disposed about the elongated member 314. The first tube segment 348 has an inner diameter that is slightly larger than the outer diameter of the elongated member 314, allowing the first filter member 316 to slide and rotate about the elongated member 314. The second tube segment 350, in turn, is fixedly secured to the elongated member 314.

Several openings or pores 332 disposed on the first and second filter membranes 316, 318 permit the perfusion of blood through the embolic protection filter 310. As with other embodiments described herein, the size of the openings on the first filter membrane may be the same as the size of the openings on the second filter membrane.

Alternatively, the size of the openings on the first filter membrane may be different than the size of the openings on the second filter membrane. In certain embodiments, the openings on the first filter membrane may be larger than the size of the openings on the second filter membrane. In use, the first filter membrane can be rotated from a first (i.e. misaligned) position to a second (i.e. aligned) position, resulting in an increase in the overall porosity of the filter. Such rotation of the first filter membrane relative to the second filter membrane can be utilized, for example, to maintain a steady flow of blood through the filter as the first filter membrane becomes clogged with embolic debris.

Figure 8:
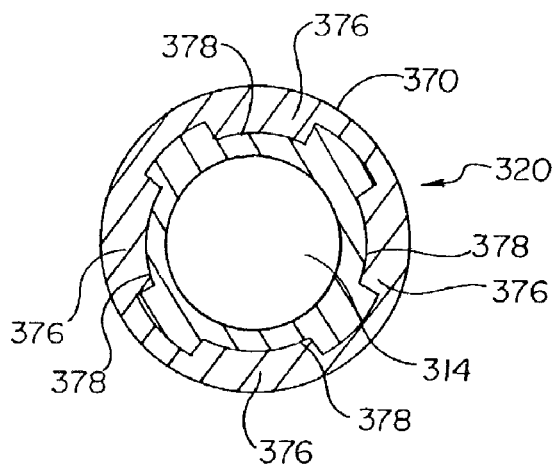
FIG. 8 is a cross-sectional view of the embolic protection filter of FIG. 7 taken along line 8-8.

Actuator mechanism 320 comprises a tubular member 370 having a proximal portion (not shown), a distal portion 372, and an inner lumen 374. As can be seen in FIG. 8, the distal portion 372 of actuator mechanism 320 includes several reduced inner diameter portions 376 configured to engage several recesses 378 formed on the filter base 350. To releasably secure the actuator mechanism 320 to the filter base 350, tubular member 370 can be rotated until the reduced inner diameter portions 376 are aligned and engaged within the recesses 378 formed on the filter base 350. Once engaged, the tubular member 370 can then be rotated, force the first filter membrane 316 to rotate relative to the second filter membrane 318.

Figure 9:
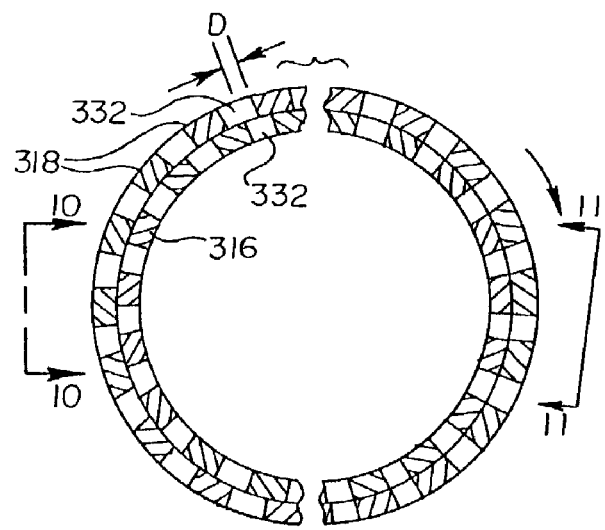
FIG. 9 is a cross-sectional view of the embolic protection of FIG. 7 taken along line 9-9.
Figure 10:
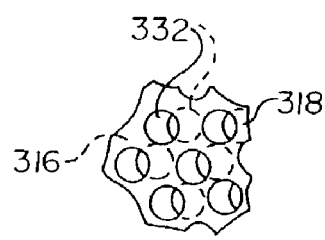
FIG. 10 is a plan view of the embolic protection filter of FIG. 7 taken along view 10-10, wherein the first and second filter membranes are shown in a first (i.e. misaligned) position.

FIG. 9 is a cross-sectional view of the embolic protection filter 310 of FIG. 7 along line 9-9, showing the relative orientation of the first and second filter membranes 316, 318 between a first (i.e. misaligned) position and a second (i.e. aligned) position. In a first position illustrated to the left in FIG. 9, the first filter membrane 316 is rotated relative to the second filter membrane 318 such that the openings 332 on each membrane 316, 318 are staggered from each other a distance D. As a result, the openings 332 on the second filter membrane 318 are partially blocked by the first filter membrane 316, as shown in FIG. 10.

Figure 11:
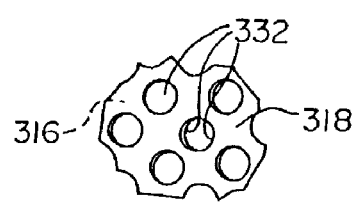
FIG. 11 is a plan view of the embolic protection filter of FIG. 7 taken along view 11-11, wherein the first and second filter membranes are shown in a second (i.e. aligned) position.

Once the openings 332 on the first filter membrane 316 become occluded with embolic debris, actuator mechanism 340 can be rotated until the openings 332 on the second filter membrane 318 are in alignment with the openings 332 on the first filter membrane 316, as illustrated to the right in FIG. 9. Once aligned, the openings 332 on the second filter membrane 318 are no longer blocked by the first filter membrane 316, as shown in FIG. 11.

Although the various embodiments described herein illustrate the use two filter membranes, other configurations have been envisioned which utilize more than two membranes. For example, an embolic protection filter in accordance with the present invention may include three or more filter membranes that can be selectively actuated within a vessel to collect and store embolic debris dislodged during a therapeutic procedure.

Having thus described the several embodiments of the present invention, those of skill in the art will readily appreciate that other embodiments may be made and used which fall within the scope of the claims attached hereto. Numerous advantages of the invention covered by this document have been set forth in the foregoing description. It will be understood that this disclosure is, in many respects, only illustrative. Changes may be made in details, particularly in matters of shape, size and arrangement of parts without exceeding the scope of the invention.

What is claimed is:

1. An embolic protection filter having a proximal end and a distal end for using during a therapeutic procedure in a patient, the filter comprising:
   a first filter membrane having a generally conical shape opening towards the proximal end coupled to an elongated member;
   a second filter membrane having a generally conical shape opening towards the proximal end coupled to the elongated member distal the first filter membrane; and
   a filter frame adapted to support the first and second filter membranes within a body lumen;
   wherein when the filter is disposed percutaneously, the first filter membrane is actuatable from an expanded position to a collapsed position independent of the second filter membrane in response to a force applied to the filter from the proximal end.

2. The embolic protection filter of claim 1, wherein said elongated member is a guidewire.

3. The embolic protection filter of claim 1, wherein said elongated member is a hypo-tube.

4. The embolic protection filter of claim 1, wherein said elongated member is a catheter.

5. The embolic protection filter of claim 1, wherein each of said first and second filter membranes comprise a microporous membrane.

6. The embolic protection filter of claim 1, wherein each of said first and second filter membranes comprise a woven or braided mesh screen.

7. The embolic protection filter of claim 1, wherein the first filter membrane includes a first set of openings, and wherein the second filter membrane includes a second set of openings.

8. The embolic protection filter of claim 7, wherein the size of the first set of openings is the same as the size of the second set of openings.

9. The embolic protection filter of claim 7, wherein the size of the first set of openings is larger than the size of the second set of openings.

10. The embolic protection filter of claim 1, wherein said filter frame comprises a plurality of support struts.

11. The embolic protection filter of claim 10, wherein said plurality of support struts are biased in an outward direction.

12. The embolic protection filter of claim 10, wherein said plurality of support struts comprise a first set of support struts and a second set of support struts.

13. The embolic protection filter of claim 10, wherein said plurality of support struts are formed of a metal.

14. The embolic protection filter of claim 13, wherein said metal is stainless steel.

15. The embolic protection filter of claim 10, wherein said plurality of support struts are formed of a shape-memory material.

16. The embolic protection filter of claim 15, wherein said shape-memory material is a nickel-titanium alloy.

17. The embolic protection filter of claim 1, further comprising an actuator mechanism.

18. An embolic protection filter having a proximal end and a distal end comprising:
   a first filter membrane having a generally conical shape opening towards the proximal end coupled to an elongated member;
   a second filter membrane having a generally conical shape opening towards the proximal end coupled to the elongated member distal the first filter membrane;
   a filter frame adapted to support the first and second filter membranes within a body lumen;
   wherein the first filter membrane is actuatable between an expanded position and a collapsed position independent of the second filter membrane in response to a force applied to the filter from the proximal end;
   further comprising an actuator mechanism; and
   wherein said actuator mechanism comprises a first retrieval member coupled to the first filter membrane, and a second retrieval member coupled to the second filter membrane.

19. The embolic protection filter of claim 18, wherein each of said first and second retrieval members comprise one or more wires.

20. The embolic protection filter of claim 18, wherein said elongated member includes a first opening configured to receive the first retrieval member, and a second opening configured to receive the second retrieval member.

21. An embolic protection filter having a proximal end and a distal end comprising:
   a first filter membrane having a generally conical shape opening towards the proximal end coupled to an elongated member;
   a second filter membrane having a generally conical shape opening towards the proximal end coupled to the elongated member distal the first filter membrane;
   a filter frame adapted to support the first and second filter membranes within a vessel;

a first actuator mechanism coupled to the first filter membrane; and a second actuator mechanism coupled to the second filter membrane;

wherein the first actuator mechanism may actuate the first filter membrane into a collapsed position independent of the second filter membrane in response to a force applied from the proximal end.

22. The embolic protection filter of claim 21, wherein said elongated member is a guidewire.

23. The embolic protection filter of claim 21, wherein said elongated member is a hypo-tube.

24. The embolic protection filter of claim 21, wherein said elongated member is a catheter.

25. The embolic protection filter of claim 21, wherein each of said first and second filter membranes comprise a microporous membrane.

26. The embolic protection filter of claim 21, wherein each of said first and second filter membranes comprise a woven or braided mesh screen.

27. The embolic protection filter of claim 21, wherein the first filter membrane includes a first set of openings, and wherein the second filter membrane includes a second set of openings.

28. The embolic protection filter of claim 27, wherein the size of the first set of openings is the same as the size of the second set of openings.

29. The embolic protection filter of claim 27, wherein the size of the first set of openings is larger than the size of the second set of openings.

30. The embolic protection filter of claim 21, wherein said filter frame comprises a plurality of support struts.

31. The embolic protection filter of claim 30, wherein said plurality of support struts are biased in an outward direction.

32. The embolic protection filter of claim 30, wherein said plurality of support struts are formed of a metal.

33. The embolic protection filter of claim 32, wherein said metal is stainless steel.

34. The embolic protection filter of claim 30, wherein said plurality of support struts are formed of a shape-memory material.

35. The embolic protection filter of claim 34, wherein said shape-memory material is a nickel-titanium alloy.

36. The embolic protection filter of claim 21, wherein said first actuator mechanism comprises a first set of retrieval members configured to engage the first filter membrane, and said second actuator mechanism comprises a second set of retrieval members configured to engage the second filter membrane.

37. The embolic protection filter of claim 36, wherein each of said first and second sets of retrieval members comprise two or more wires.

38. The embolic protection filter of claim 36, wherein said elongated member includes a first opening configured to receive the first set of retrieval members, and a second opening configured to receive the second set of retrieval members.

39. An embolic protection device having a proximal end and a distal end, comprising:

a guidewire;

a filter coupled to the guidewire, the filter including a first filter membrane having a generally conical shape opening towards the proximal end, a second filter membrane having a generally conical shape opening towards the proximal end, and a filter frame adapted to support the first and second filter membranes within a body lumen, the filter frame including a plurality of support struts;

a actuator mechanism for selectively actuating the first or second filter membranes;

wherein the first filter membrane is actuatable from an expanded position to a collapsed position independent of the second filter membrane in response to a force applied from the proximal end.

40. The embolic protection filter of claim 39, wherein the plurality of support struts are biased in an outward direction.

41. The embolic protection filter of claim 39, wherein the filter is slidably and rotatably coupled to the guidewire.

* * * * *